United States Patent [19]
Gibson et al.

[11] Patent Number: 6,119,506
[45] Date of Patent: Sep. 19, 2000

[54] APPARATUS AND METHOD FOR DETERMINING TRANSPORT PROPERTIES OF POROUS MATERIALS

[75] Inventors: Phillip W. Gibson, Holliston; Cyrus E. Kendrick, Stow; Donald Rivin, Natick, all of Mass.

[73] Assignee: The United States of America as represented by the Secretary of the Army, Washington, D.C.

[21] Appl. No.: 09/368,156

[22] Filed: Aug. 4, 1999

Related U.S. Application Data

[63] Continuation of application No. 09/094,877, Jun. 15, 1998, abandoned.

[51] Int. Cl.[7] .......................... G01N 15/08; G01N 13/04; C12Q 1/02; B01L 3/00
[52] U.S. Cl. .................................. 73/38; 73/37; 73/64.47; 73/159; 73/37.7; 34/89; 435/297.2; 436/178
[58] Field of Search .......................... 73/38, 64.47, 37.7, 73/159, 40, 37, 73; 34/89; 435/29, 287.1, 287.9, 297.2, 297.1; 436/108, 121, 178

[56] References Cited

U.S. PATENT DOCUMENTS

| | | | |
|---|---|---|---|
| 2,716,886 | 9/1955 | Rowe | 73/53 |
| 3,195,346 | 7/1965 | Ehrmantraut et al. | 73/53 |
| 3,318,138 | 5/1967 | Rolfson | 73/64.3 |
| 3,590,634 | 7/1971 | Pasternak et al. | 73/159 |
| 4,028,931 | 6/1977 | Bisera et al. | 73/64.3 |
| 4,064,740 | 12/1977 | Crosby, Jr. | 73/38 |
| 4,150,564 | 4/1979 | Barlow et al. | 73/64.3 |
| 4,191,046 | 3/1980 | Baker et al. | 73/38 |
| 4,198,853 | 4/1980 | Graham | 73/38 |
| 4,198,854 | 4/1980 | Washington et al. | 73/38 |
| 4,287,754 | 9/1981 | Heitmann et al. | 73/38 |
| 4,311,037 | 1/1982 | Gotchel et al. | 73/38 |
| 4,385,517 | 5/1983 | Sorce et al. | 73/38 |
| 4,464,927 | 8/1984 | Reid | 73/38 |
| 4,481,808 | 11/1984 | Sakata et al. | 73/61.1 R |
| 4,506,542 | 3/1985 | Rose | 73/38 |
| 4,536,971 | 8/1985 | Pulsmeier et al. | 34/89 |
| 4,557,138 | 12/1985 | Dumitriu-Valcea | 73/38 |
| 4,656,865 | 4/1987 | Callan | 73/38 |
| 4,663,969 | 5/1987 | Bibby et al. | 73/159 |
| 4,852,389 | 8/1989 | Mayer et al. | 73/38 |
| 4,918,981 | 4/1990 | Gore | 73/76 |
| 4,944,180 | 7/1990 | Tou et al. | 73/38 |
| 5,005,403 | 4/1991 | Steudle et al. | 73/64.3 |
| 5,107,696 | 4/1992 | Mayer | 73/38 |
| 5,141,873 | 8/1992 | Steudle et al. | 436/148 |
| 5,157,960 | 10/1992 | Brehm | 73/38 |
| 5,278,501 | 1/1994 | Guilfoyle | 324/303 |
| 5,411,888 | 5/1995 | Gordon et al. | 436/5 |
| 5,537,868 | 7/1996 | Sofner | 73/160 |
| 5,599,688 | 2/1997 | Grass | 435/29 |
| 5,659,130 | 8/1997 | Chung et al. | 73/64.47 |
| 5,738,826 | 4/1998 | Lloyd | 422/102 |

*Primary Examiner*—Hezron Williams
*Assistant Examiner*—J. David Wiggins
*Attorney, Agent, or Firm*—Vincent J. Ranucci

[57] ABSTRACT

An apparatus and method for measuring the mass transport properties of porous materials. The apparatus is a permeation or diffusion cell that comprises two outer portions with longitudinal channels therein, two clamping plates with openings therein, two flow inlets and two flow outlets in fluid communication with such outer portion channels, which cell retains a sample of porous material during measurement procedures. In one embodiment, the apparatus is configured for measuring pure diffusion transport properties of the sample of porous material. In another embodiment, the apparatus is configured for measuring the diffusion and convection transport properties of the sample of porous material. In a further embodiment, the apparatus is configured for measuring the pure convection transport properties of the sample of porous material.

27 Claims, 10 Drawing Sheets

5,119,506

APPARATUS AND METHOD FOR DETERMINING TRANSPORT PROPERTIES OF POROUS MATERIALS

This application is a continuation of application Ser. No. 09/094,877, filed on Jun. 15, 1998 now abandoned.

The invention described herein may be manufactured, used and licensed by or for the Government for Governmental purposes without the payment to us of any royalty thereon.

BACKGROUND OF THE INVENTION

1. Field of the Invention

The present invention generally relates to an apparatus and method for determining the transport properties of porous materials.

2. Problem to be Solved

During the manufacture of porous materials such as textiles, the porous materials are typically tested to determine transport properties such as diffusion, diffusion/convection and pure gas convection. Typically, a sample of the porous material is used to determine the aforementioned properties. Conventional systems and methods for determining the aforementioned properties typically require that a new sample of porous material be used to determine each of the specific properties. Changing samples for each test significantly decreases the amount of tests that can be conducted during a given unit of time. As a result, the time required for quality testing significantly increases thereby increasing overall production time and costs.

It is therefore an object of the present invention to provide a new and improved apparatus to facilitate repetitive measurements of mass transport properties of porous materials using a single relatively small specimen.

It is another object of the present invention to provide a method for determining the transport properties of porous materials that is less time consuming than conventional methods.

Other objects and advantages of the present invention will be apparent to one of ordinary skill in the art in light of the ensuing description of the present invention.

SUMMARY OF THE INVENTION

The present invention is directed to, in one aspect, an apparatus for retaining a sample of porous material comprising a first portion, a second portion, a first clamping plate and a second clamping plate. The first portion comprises an exterior side, an interior side and a substantially longitudinally extending channel formed in the interior side. The first portion has at least one port extending from the exterior side to the interior side and in fluid communication with the channel. The first portion further comprises a flow inlet and a flow outlet in communication with the channel. The first clamping plate has a first side for contacting the interior side of the first portion and a second side for contacting a sample of porous material. The first clamping plate has an opening that is substantially aligned with the channel of the first portion. The second clamping plate has a first side and a second side for contacting a sample of porous material. The second clamping plate has an opening that is substantially aligned with the opening of the first clamping plate. The second portion has an exterior side and an interior side for contacting the first side of the second clamping plate. The second portion includes a substantially longitudinally extending channel formed in the interior side of the second portion. The second portion further includes at least one port extending from the exterior side of the second portion to the interior side of the second portion and in fluid communication with the channel formed in the interior side of the second portion. The second portion further includes a flow inlet and flow outlet in communication with the channel of the second portion.

In another aspect, the present invention is directed to a method for measuring the pure diffusion transport properties of a sample of porous material comprising:

(a) providing a cell for retaining the sample of porous material, the cell comprising (i) a first portion comprising an exterior side and an interior side, the first portion having a substantially longitudinally extending channel formed in the interior side, the first portion having at least one port extending from the exterior side to the interior side and in communication with the channel, the first portion further comprising a flow inlet and a flow outlet in communication with the channel, (ii) a first clamping plate having a first side for contacting the interior side of the first portion and a second side for contacting a sample of porous material, the first clamping plate having an opening that is substantially aligned with the channel of the first portion, (iii) a second clamping plate having a first side, the second clamping plate further comprising a second side for contacting a sample of porous material, the second clamping plate having an opening that is substantially aligned with the opening of the first clamping plate, and (iv) a second portion having an exterior side and an interior side for contacting the first side of the second clamping plate, the second portion having a substantially longitudinally extending channel formed in the interior side of the second portion, the second portion further including at least one port extending from the exterior side of the second portion to the interior side of the second portion and in communication with the channel formed in the interior side of the second portion, the second portion further comprising a flow inlet and a flow outlet in communication with the channel of the second portion;

(b) flowing gas streams that represent different porous sample medium conditions into the flow inlets of the first and second portions, each of the gas streams different sample conditions represented, respectively, by one of a having a dry gas portion, a water-saturated portion and a predetermined relative humidity;

(c) maintaining the pressure drop across the sample of porous material at zero so that transport occurs substantially by pure diffusion;

(d) measuring the flux of water vapor diffusing through the sample of porous material;

(e) varying the relative humidity of the nitrogen streams flowing into the flow inlets of the first and second portions; and (f) repeating steps (b)–(e) to include respective measurements for each of the above stated porous sample medium conditions including a dry gas portion, a water-saturated portion, and a sequential set of different predetermined relative humidities.

In a further aspect, the present invention is directed to a method for measuring the diffusion and convection transport properties of a sample of porous material comprising:

(a) providing an cell for retaining the sample of porous material, the cell comprising (i) a first portion comprising an exterior side and an interior side, the first portion having a substantially longitudinally extending channel formed in the interior side, the first portion having at least one port extending from the exterior side to the interior side and in communication with the channel, the first portion further comprising a flow inlet and a flow outlet in communication with the channel, (ii) a first clamping plate having a first side for contacting the interior side of the first portion and a second side for contacting a sample of porous material, the first clamping plate having an opening that is substantially aligned with the channel of the first portion, (iii) a second clamping plate having a first side, the second clamping plate further comprising a second side for contacting a sample of porous material, the second clamping plate having an opening that is substantially aligned with the opening of the first clamping plate, and (iv) a second portion having an exterior side and an interior side for contacting the first side of the second clamping plate, the second portion having a substantially longitudinally extending channel formed in the interior side of the second portion, the second portion further including at least one port extending from the exterior side of the second portion to the interior side of the second portion and in communication with the channel formed in the interior side of the second portion, the second portion further comprising a flow inlet and a flow outlet in communication with the channel of the second portion;

(b) flowing gas streams that represent different porous sample medium conditions into the flow inlets of the first and second portions, each of the gas streams different sample conditions represented, respectively, by one of a having a dry gas portion, a water-saturated gas portion and a predetermined relative humidity;

(c) creating a pressure drop across the sample of porous material so that transport occurs by diffusion and convection;

(d) measuring the relative humidity of the gas streams flowing from the flow outlets of the upper and lower portions;

(e) increasing the pressure drop across the sample of porous material;

(f) measuring mass flow rate of the gas stream flowing from the flow outlet of the lower portion; and (g) repeating steps (b)–(f) to include respective measurements for each of the above stated porous sample medium conditions including a dry gas portion, a water-saturated portion, and a sequential set of different predetermined relative humidities.

Pure convection is determined by subtracting diffusive flow ($\Delta P=0$) from convective and diffusive flow. In a further aspect, the present invention is directed to a method for measuring the humidity-dependent convective transport properties of the sample of porous material. The method comprises the steps of:

(a) providing a cell for retaining the sample of porous material, the cell comprising (i) a first portion comprising an exterior side and an interior side, the first portion having a substantially longitudinally extending channel formed in the interior side, the first portion having at least one port extending from the exterior side to the interior side and in communication with the channel, the first portion further comprising a flow inlet and a flow outlet in communication with the channel, (ii) a first clamping plate having a first side for contacting the interior side of the first portion and a second side for contacting a sample of porous material, the first clamping plate having an opening that is substantially aligned with the channel of the first portion, (iii) a second clamping plate having a first side, the second clamping plate further comprising a second side for contacting a sample of porous material, the second clamping plate having an opening that is substantially aligned with the opening of the first clamping plate, and (iv) a second portion having an exterior side and an interior side for contacting the first side of the second clamping plate, the second portion having a substantially longitudinally extending channel formed in the interior side of the second portion, the second portion further including at least one port extending from the exterior side of the second portion to the interior side of the second portion and in communication with the channel formed in the interior side of the second portion, the second portion further comprising a flow inlet and a flow outlet in communication with the channel of the second portion;

(b) closing the flow inlet of the second portion;

(c) closing the flow outlet of the first portion;

(d) flowing a gas stream that represents different porous sample medium conditions into the flow inlet of the first portion, each of the different sample conditions represented, respectively, by one of a gas stream having a dry gas portion, a water-saturated gas portion and a predetermined relative humidity;

(e) measuring the pressure drop across the sample of porous material as a function of flow rate and relative humidity;

(f) varying the relative humidity of the gas stream; and (g) repeating steps (b)–(f) to include respective measurements for each of the above stated porous sample medium conditions including a dry gas portion, a water-saturated portion, and a sequential set of different predetermined relative humidities.

BRIEF DESCRIPTION OF THE DRAWINGS

The features of the invention are believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DETAILED DESCRIPTION OF THE INVENTION

In describing the preferred embodiments of the present invention, reference will be made herein to FIGS. 1–12 of the drawings in which like numerals refer to like features of the invention.

Figure 2:
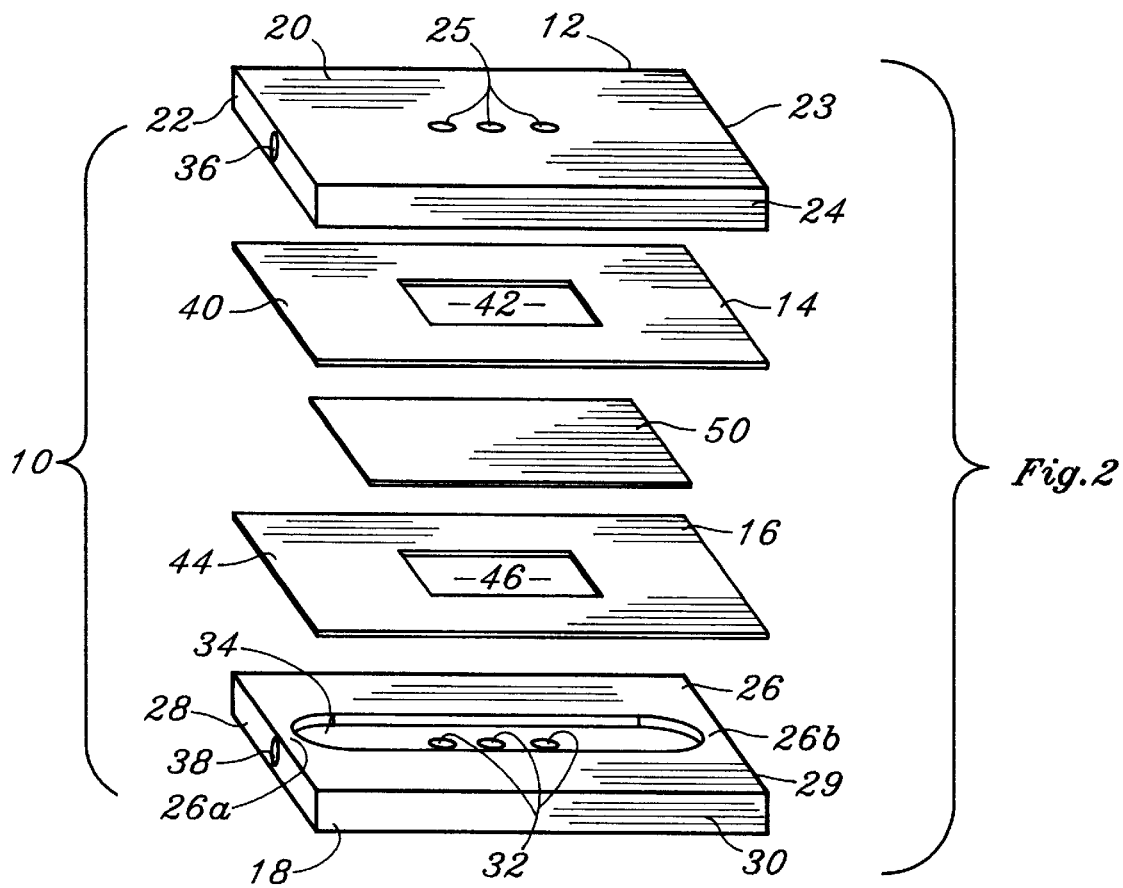
FIG. 2 is an exploded view of a cell of the present invention, depicted in FIG. 1, for retaining samples of porous material.

Referring to FIG. 2, apparatus 10 of the present invention is a moisture permeation cell that retains a sample of porous material therein so that measurements can be conducted to determine diffusion, diffusion/convection and humidity-dependent gas convection properties of the porous material. Cell 10 comprises an upper portion 12, an upper sample clamping plate 14, a lower sample clamping plate 16 and a lower portion 18. The lower and upper portions 12 and 18, respectively, are substantially identical in construction. The upper portion 12 has an exterior side 20, an interior side (not shown), widthwise ends 22 and 23 and a lengthwise end 24 (the opposite lengthwise end not shown). In one embodiment, the upper and lower portions 12 and 18, respectively, and the upper and lower clamping plates 14 and 16, respectively, are substantially square shaped. In another embodiment, the upper and lower portions 12 and 18, respectively, and the upper and lower clamping plates 14 and 16, respectively, have a rectangular shape. However, it is to be understood that the upper and lower portions 12 and 18, respectively, and the upper and lower clamping plates 14 and 16 can have other geometric shapes. In a preferred embodiment, the upper and lower portions 12 and 18, respectively, and the upper and lower clamping plates 14 and 16 are fabricated from corrosion-resistant materials, e.g. stainless steel, aluminum, plastic, etc.

Referring to FIG. 2, the upper portion 12 has a plurality of ports or openings 25 formed therein. In a preferred embodiment, the ports 25 are longitudinally arranged and located substantially in the center of the upper portion 12. The ports 25 are used for the measurement of differential pressure. This will be discussed in detail below. Similarly, the lower portion 18 has an exterior side (not shown), an interior side 26, widthwise ends 28, 29 and a lengthwise end 30 (the opposite lengthwise end not shown). The lower portion 18 has a plurality of ports or openings 32 formed therein. In a preferred embodiment, the ports or openings 32 are longitudinally arranged and are located substantially in the center of the lower portion 18. Ports or openings 32 function in the same manner as ports 25 in the upper portion 12.

Referring to FIG. 2, the upper portion 12 includes a longitudinally oriented duct or channel (not shown). Similarly, the lower portion 18 includes a longitudinally oriented duct or channel 34. The ensuing description is in terms of the channel 34 of the lower portion 18 since the channel of the upper portion 12 is not shown. However, it is to be understood that the ensuing description is also applicable to the duct or channel that is formed in the upper portion 12. The duct or channel 34 is equidistant from the lengthwise end 29 and the opposite lengthwise end 30. The channel 34 extends for substantially the entire length of the lower portion 18 and is between the portions 26a and 26b of interior side 26.

As shown in FIG. 2, the upper portion 12 includes an opening or port 36 formed in the widthwise end 22 and which is in fluid and gaseous communication with the channel (not shown) formed in the upper portion 12. The upper portion 12 also has another opening (not shown) formed in the opposite widthwise end 23 that is in fluid and gaseous communication with the channel (not shown) in the upper portion 12. The opening 36 and the other opening (not shown) function as gas flow outlets or inlets, depending upon how the cell 10 is oriented with respect to other components of a test system. Similarly, the lower portion 18 includes an opening or port 38 formed in the widthwise end 28 and which is in fluid and gaseous communication with the channel 34 formed in the lower portion 18. The lower portion 18 also has another opening (not shown) formed in the opposite widthwise end 29 that is in fluid and gaseous communication with the channel 34 formed in the lower portion 18. The opening 38 of the lower portion 18 and the other opening in the opposite widthwise end 29 function as flow outlets or inlets, depending upon how the cell 10 is oriented with respect to other components of a test system.

Referring to FIG. 2, in one embodiment, the shape and dimensions of duct 34 and the duct formed in the upper portion 12 induce laminar flow of gases flowing through cell 10. This will be further discussed below. In one embodiment, each duct has a width of about 0.025 meter, a height of about 0.0025 meter, and a length of about 0.13 meter. However, it is to be understood that the ducts in the upper and lower portions 12 and 18, respectively, may have other dimensions depending upon the test requirements. For example, in another embodiment, each duct may have a height of 0.0050 meter with all the remaining dimensions being the same as described above.

Referring to FIG. 2, the upper sample clamping plate 14 has a top surface 40 and a bottom surface (not shown). The plate 14 further includes an opening 42. The size, shape and location of the opening 42 may vary depending upon the overall dimensions of the cell 10. FIG. 2 shows one example wherein the opening 42 is located substantially in the center of the sample clamping plate 14 and has a substantially square shape. In one embodiment, the area of the opening 42 is 0.001 square meter. However, the opening 42 may have other dimensions as well. The lower sample plate 16 is substantially identical in construction to the upper sample clamping plate 14. Specifically, the lower sample clamping plate 16 has a top surface 44 and a bottom surface (not shown). The clamping plate 16 further includes an opening 46. The size, shape and location of the opening can be altered depending upon the overall dimensions of the cell 10. FIG. 2 shows one example wherein the opening 46 is located substantially in the center of the sample clamping plate 16 and has a substantially square shape. In one embodiment, the area of the opening 46 is 0.001 square meter. However, the opening 46 may have other dimensions as well. As shown in FIG. 2, the sample of porous material 50 is disposed between the upper sample clamping plate 14 and the lower sample clamping plate 16. In one embodiment, the dimensions of the channels formed in the upper and lower portions 12 and 18, respectively, and of the openings 42 and 46 formed in the sample clamping plates 14 and 16, respectively, are configured to provide flow velocities of at least 0.5 m/sec over the sample to minimize the contribution of boundary air layer resistances to test measurements. However, it is to be understood that cell 10 can be configured to provide other flow velocities.

The actual positioning of the sample of porous material 50 between the sample clamping plates 14 and 16, as shown in FIG. 2, depends upon the type of porous material being tested. The upper and lower portions 14 and 16, respectively, are clamped together to form a fluid or gas tight relationship between the portions 14 and 16 so as to prevent leaking. Sealing gaskets (not shown) may be used between the upper and lower portions 12 and 18, respectively, depending upon the porous material being tested. For relatively thick porous materials that are highly permeable, other types of sealing methods may be used. For example, the edges of the upper portion 12 and lower portion 18 may be sealed with molten wax. In another example, the edges of the upper portion 12 and lower portion 18 may be sealed with a curable sealant.

Figure 1:
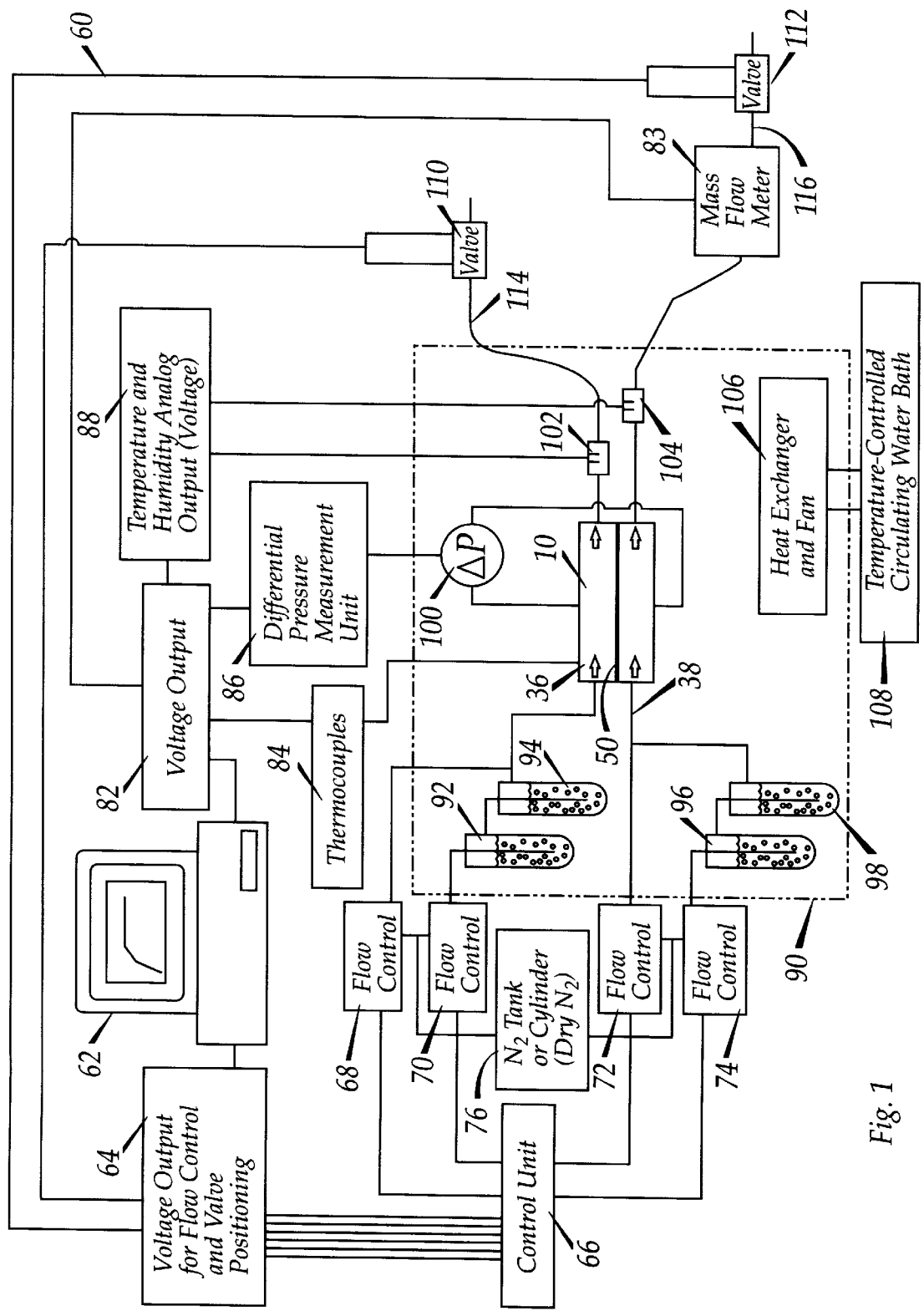
FIG. 1 is a block diagram of a system of the present invention which is used for determining the transport properties of porous materials.

Referring to FIG. 1, the system 60 measures the transport properties of porous materials. The system uses a personal computer 62 that has a general purpose instrumentation bus (GPIB). The personal computer 62 is controlled by test personnel and executes a software program that implements particular steps to control the various components in the system 60. The personal computer 62 includes a digital-to-analog converter ("DAC") and an analog-to-digital converter ("ADC"). The personal computer 62 outputs digital signals that represent a particular voltage level. These digital signals are inputted into a voltage output module 64. In response to these digital signals, the voltage output module 64 outputs voltage signals having predetermined magnitudes for input into a control unit 66 that controls mass flow control modules 68, 70, 72 and 74. Each of the mass flow control modules 68, 70, 72 and 74 has an input that is gaseously connected to gas storage supply device 76. In embodiment, device 76 is a nitrogen $N_2$ storage supply device. However, it is to be understood that device 76 may be configured to store other inert gases or dry air.

As shown in FIG. 1, the system 60 further includes a voltage interface module 82 that receives analog voltages from a mass flow meter 83, thermocouples 84, a differential pressure measurement unit 86 and a temperature and humidity analog output voltage module 88. Differential pressure measurement unit 86 conditions the signals received from the transducer 100. The voltage interface module 82 includes a multiplexor that is controlled by a digital signal from the personal computer 62. The multiplexor transfers the signals received from mass flow meter 83, the thermocouples 84, the differential pressure measurement unit 86, and the temperature and humidity analog output voltage module 88 to the personal computer 62. The output of the voltage interface module 82 is inputted into the ADC input of the personal computer 62. The ADC converts the analog signals into digital signals for use by processing circuitry within the personal computer 62. As a result of such processing, the measured quantities, e.g. differential pressure, temperature, humidity, etc. are displayed on the screen of the personal computer.

As shown in FIG. 1, the system 60 further includes an insulated chamber 90. Within the insulated chamber 90, are cell 10, saturated $N_2$ bubblers 92, 94, 96, and 98, differential pressure transducer 100, a pair of humidity probes 102 and 104, and a heat exchanger unit 106. The heat exchanger unit 106 includes a fan and is fluidly coupled to a temperature-controlled circulating water bath 108 that is located outside the insulated chamber 90.

Referring to FIG. 1, the output of the flow controller 70 is inputted into the bubbler 92. The output of bubbler 92 is inputted into bubbler 94. The output of flow controller 68 is combined with the output of bubbler 94. These combined gases are flowed into flow inlet 36 of the upper portion 12 of the cell 10. Similarly, the output of the flow controller 74 is inputted into the bubbler 96. The output of bubbler 96 is inputted into bubbler 98. The output of flow controller 72 is combined with the output of bubbler 98. These combined gases are flowed into flow inlet 38 of the lower portion 18 of the cell 10.

Referring to FIG. 1, differential pressure transducer 100 has a pair of inputs that are gaseously connected to the ports 25 and 32 formed in the upper and lower portions 12 and 18, respectively, of the cell 10. The flow outlet (not shown) of the upper portion 12 of the cell 10 is gaseously connected to a humidity probe 102. Similarly, the flow outlet (not shown) of the lower portion 18 of the cell 10 is gaseously connected to the humidity probe 104. The heat exchanger 106 cooperates with the temperature-controlled circulating bath 108 to provide a predetermined temperature within the insulated chamber 90. System 60 further includes automatically controlled valves 110 and 112 that receive control signals from voltage output module 64. Valve 110 has an input 114 gaseously connected to an outlet of the humidity probe 102. Valve 112 has an input 116 that is gaseously connected to the output of the mass flow meter 83. Mass flow meter 83 has an input that is gaseously connected to an outlet of the humidity probe 104.

In a preferred embodiment, mass flow controllers 68, 70, 72 and 74 are configured as a Model 1259C Mass Flow Controller with a Model 247C 4 Channel Readout, both of which being manufactured by MKS Instruments, Inc. of Andover, Mass. In a preferred embodiment, the electronic mass flow meter 76 has the operational characteristics of the Model 822 Top-Trak mass flow meter manufactured by Sierra Instruments, Inc. of Monterey, Calif. In a preferred embodiment, the humidity probes 102 and 104 have the operating characteristics of the Model HMI 32 humidity probe with a Model HMP 35 Sensor, both of which being manufactured by Vaisala, Inc. of Woburn, Mass. The Model HMI 32 humidity probe is a capacitance-type probe. In a preferred embodiment, the differential pressure transducer 100 has the operational characteristics of a Baratron Type 398 differential pressure transducer manufacture by MKS Industries, Inc. In a preferred embodiment, the differential pressure measurement module 86 has the operational characteristics of the Type 270B signal conditioner manufactured by MKS Instruments, Inc.

Although the methods of the present invention are described below as using nitrogen streams, it is to be understood that instead of nitrogen, other inert gases can be used. Furthermore, dry air can be used in place of inert gases.

1. Determining Pure Diffusion

In order to determine pure diffusion properties of a porous material, the following steps are implemented. Referring to FIG. 1, the user inputs into the computer 62 a predetermined number of desired humidity set-points for the upper and lower nitrogen streams flowing into the cell 10. For example, the user may input up to 20 desired humidity set-points. Next, nitrogen streams consisting of a mixture of dry nitrogen and water-saturated nitrogen are flowed into the inlets 36 and 38 of the upper and lower portions 12 and 18, respectively, of cell 10. The computer 62 uses the predetermined setpoint voltage control each of the flow controllers 68, 70, 72 and 74 in order to produce the desired relative humidity in the upper and lower nitrogen streams. Specifically, the computer 62 outputs signals to the voltage output module 64. In response, voltage output module 64 outputs control signals to control the flow controls 68, 70, 72 and 74 in order to control the proportion of the saturated and the dry components of the nitrogen streams entering cell 10. As a result, the relative humidity of the nitrogen streams is varied. The nitrogen streams pass through the channel (not shown) of portion 12 and channel 34 of lower portion 18. Thus, the nitrogen streams pass over the top and bottom surfaces of the sample of porous material 50 that is positioned between the sample clamping plates 14 and 16. (see FIG. 2). At constant mass flow, the true volumetric flow rate will vary with temperature. In a preferred embodiment, the flow rate set by the control 66 is indicated in terms of volumetric flow rates at standard conditions of 0° C. and atmospheric pressure ($1.01325 \times 10^5$ Pa). Assuming ideal gas behavior, the actual volumetric flow rate at different temperatures may be found from the mass flow rate, the temperature, and the pressure of the actual flow.

The humidity probes 102 and 104 provide output signals that represent the temperature and water vapor concentration of the nitrogen streams flowing from the flow outlets of the cell 10. These signals are inputted into the temperature and humidity module 88 which conditions the signals and outputs the conditioned signals to the digital voltmeter 82. The digital voltmeter 82 outputs digital signals representing the values measured by the humidity probes 102 and 104 onto the GPIB for input into the computer 62. The flux of water vapor diffusing through the sample 50 is determined by the signals outputted by the humidity probes 102 and 104. The computer plots the relative humidity, displays the plots on the computer screen, records the data to a computer storage disk, and applies operator-determined equilibration criteria to determine when equilibrium has been reached for that set point. Once equilibrium is attained, the results, i.e. humidity, calculated flux, etc., are outputted to a printer and to a data file on the storage disk. The computer then proceeds to the next set point and repeats the process.

As shown in FIG. 1, the humidity probes 102 and 104 effect measurements of the nitrogen stream flowing through the duct (not shown) formed in the top portion 12 and through duct 34 of the bottom portion 18 thereby allowing two measurements of water vapor flux to be made simultaneously. The personal computer 62 determines the incoming water vapor concentration by determining the ratio of the mass flows of the saturated and dry nitrogen streams. The personal computer 62 also determines the water vapor concentration in the outgoing air stream by converting the known values of relative humidity and temperature to water vapor concentration. The computer 62 determines the mass flow rate of water vapor diffusing through the sample of porous material, from one side of cell 10 to the other, using the following formula:

$$m/A = Q(\delta C)/A = Q(C_2 - C_1)/A \tag{1}$$

wherein:

m is the mass flux of water vapor across the sample of porous material (kg/s);

A is the area of the sample of porous material (m$^2$);

Q is the volumetric flow rate through top or bottom portion of the cell (m$^3$/s); and $\delta C = C_2 - C_1$, the water vapor concentration difference, expressed in (kg/m$^3$), between incoming stream $C_1$ and outgoing stream $C_2$ in the upper portion 12 and the lower portion 18, respectively, of the cell 10.

The incoming water vapor concentration is determined by the ratio of the mass flows of the saturated and the dry nitrogen streams. As described above, the mass flow rates are controlled by the mass flow controllers 68, 70, 72 and 74. The computer 62 determines the actual volumetric flow rate at different temperatures from the mass flow rate, the temperature and the pressure of the actual flow. In order to obtain the water vapor concentration $C_2$ of the nitrogen stream flowing out of the flow outlets 36 and 38, the computer 62 converts the known values of relative humidity and temperature to water vapor concentration. The computer 62 determines the water vapor transmission rate in terms of the indicated volumetric flow rate at standard conditions, the humidity difference, and the temperature using the following formula:

$$m/A = (\delta \phi Q_s P_s M_W)/ART_s \tag{2}$$

wherein:

$M_W$ is the molecular weight of water vapor (18.015 kg/kg mole);

$Q_s$ is the volume flow rate at standard conditions of 0° C. and atmospheric pressure (m$^3$/s);

R is the universal gas constant (8314.5 N·m/kg·° K);

$T_S$ is the reference temperature at standard conditions of 0° C. in degrees K (273.15 K);

$p_s$ is the saturation vapor pressure of water (Pa);

$\delta \phi = \phi_2 - \phi_1$, the relative humidity difference between incoming stream ($\phi_1$) and the outgoing stream ($\phi_2$) in the top or bottom portion of the moisture permeation cell;

$\phi = p_v/p_s$, the relative humidity; and $p_v$ = the vapor pressure of water (Pa).

The pressure drop across the sample of porous material 50 is monitored by means of the differential pressure transducer 100 and the differential pressure measurement unit 86. In a preferred embodiment, the pressure drop across the sample 50 is maintained at zero when testing porous materials that are permeable to convective flows in order to make sure that water vapor transport takes place only by pure diffusion. The pressure drop is continuously monitored, and is controlled by means of the valves 110 and 112.

Materials that have a constant mass transfer coefficient show a linear slope on plots of flux versus concentration difference across the sample. These types of materials do not change their transport properties as a function of water content or test conditions. For materials that do not have a constant slope, the data points for a test series do not superimpose but instead form a set of curves for each test condition. In order to determine a diffusion resistance for these materials, the flux versus concentration difference curve is evaluated at various points to derive values for material diffusion resistance which will be a function of the concentration of water in the material.

A total resistance to mass transfer is defined as the simple addition of an intrinsic diffusion resistance due to the sample ($R_t$) and the diffusion resistance of the boundary air layers ($R_{bi}$):

$$m/A = h_m(\Delta \bar{C}) = (\Delta \bar{C}/(R_f + R_{bi})) \quad (3)$$

wherein:

$$R_f = [\Delta \bar{C}/(m/A)] - R_{bi} \quad (4)$$

and $h_m = [1/(R_f + R_{bi})]$ = mass transfer coefficient (m/s);
$\Delta \bar{C}$ = log mean concentration difference between top and bottom nitrogen streams (Kg/m$^3$);
$R_f$ = intrinsic diffusion resistance of sample (s/m); and
$R_{bi}$ = diffusion resistance of boundary air layers (s/m).

The log mean concentration difference across the sample is appropriate since there is significant change in the concentration of the gas stream both below and above the sample 50. In addition, the gas streams may not necessarily be in parallel flow, but may run in counter flow to maintain a more constant concentration gradient across the sample 50. The log mean concentration difference is defined as:

$$\Delta \bar{C} = (\Delta C_a - \Delta C_b)/ln(\Delta C_a/\Delta C_b) \quad (5)$$

wherein:

$\Delta C_a$ = concentration difference between the two gas streams at one end of the cell 10; and
$\Delta C_b$ = concentration difference between the two gas streams at the other end of the cell 10.

For parallel flow, the concentration differences are between the top and bottom incoming flow into the inlets 36 and 38 of cell 10 ($\Delta C_a$) and the difference between the top and bottom flows from the flow outlets of cell 10 ($\Delta C_b$). For counter-current flow, the concentration differences are between the incoming and outgoing flows at one end of the cell 10 ($\Delta C_a$), and the incoming and outgoing flows at the other end of the cell 10 ($\Delta C_b$).

Figure 3:
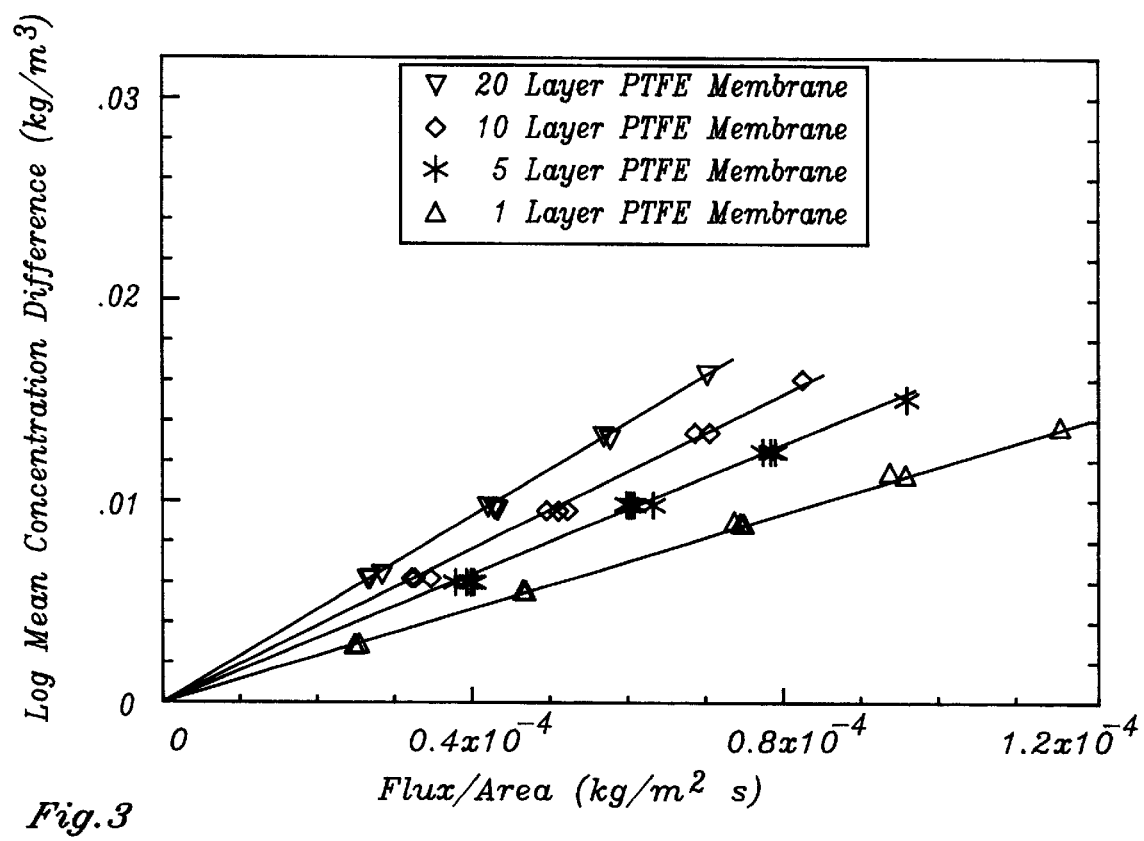
FIG. 3 is a plot of flux versus concentration for multiple layers of a PTFE membrane retained by the cell of FIG. 2.

In a preferred embodiment, a calibration or reference material is used to check the operation of the system. Preferably, a microporous polytetrafluorethylene (PTFE) membrane is used to calibrate the system because it has a relatively low resistance to water vapor diffusion but a relatively high resistance to convective flow due to the very small pore sizes. The membrane may be layered to produce a material with a lower effective diffusivity. Since diffusion takes place only through the pore spaces of the membrane, the material has a very linear and reproducible plot of flux versus concentration difference. The plot of flux versus concentration difference may be used as a calibration curve for the cell, and may also be used to determine the boundary air layer resistance present in the cell 10. FIG. 3 shows the plot of flux versus concentration difference for samples of porous material made of microporous PTFE membranes.

Since the PTFE membranes are microporous and transport occurs only through the interconnected air spaces of the membrane, the plot of the mass flux versus the concentration difference across the sample will be linear, as shown in FIG. 3. The linear plots shown in FIG. 3 include all the test results from the nine (9) different test conditions superimposed on the same constant slope line, thereby proving that the diffusion resistance of each sample is constant.

The series of tests on the microporous PTFE membranes are used to derive an estimate of the boundary layer resistance on both the top and bottom of the samples of PTFE membranes. The resistance of the sample and the boundary air layers is equal to the slope of the line for each sample of PTFE membrane in FIG. 3. For these types of materials, it can be assumed that the mass transfer resistance is additive, i.e. the resistance of the twenty (20) layers is twice the resistance of ten (10) layers. A value for the boundary air layer resistance is defined by the relationship:

$$R_{bi} = R_{total} - nR_{1-layer}; \quad (6)$$

wherein:

$R_{total}$ = measured mass transfer resistance of sample (s/m);
n = number of teflon layers; and
$R_{1-layer}$ = calculated-resistance of 1 PTFE layer (s/m).

Using the relationships shown above, the boundary air layer resistance ($R_{bi}$) for the flow conditions of FIG. 3 is about 100 s/m, and the resistance of a single layer of the PTFE membrane is about 6 s/m. The boundary air layer resistance is fairly constant at a given set of flow conditions. The total resistance of a single layer of the PTFE membrane is within 5% of the boundary air layer resistance, and thereby serves as a convenient way to directly measure the boundary layer resistance present within the cell 10 at other flow conditions. If corrected for the resistance of the single PTFE layer, it serves as a standard reference material to check the results generated by the cell 10.

Figure 4:
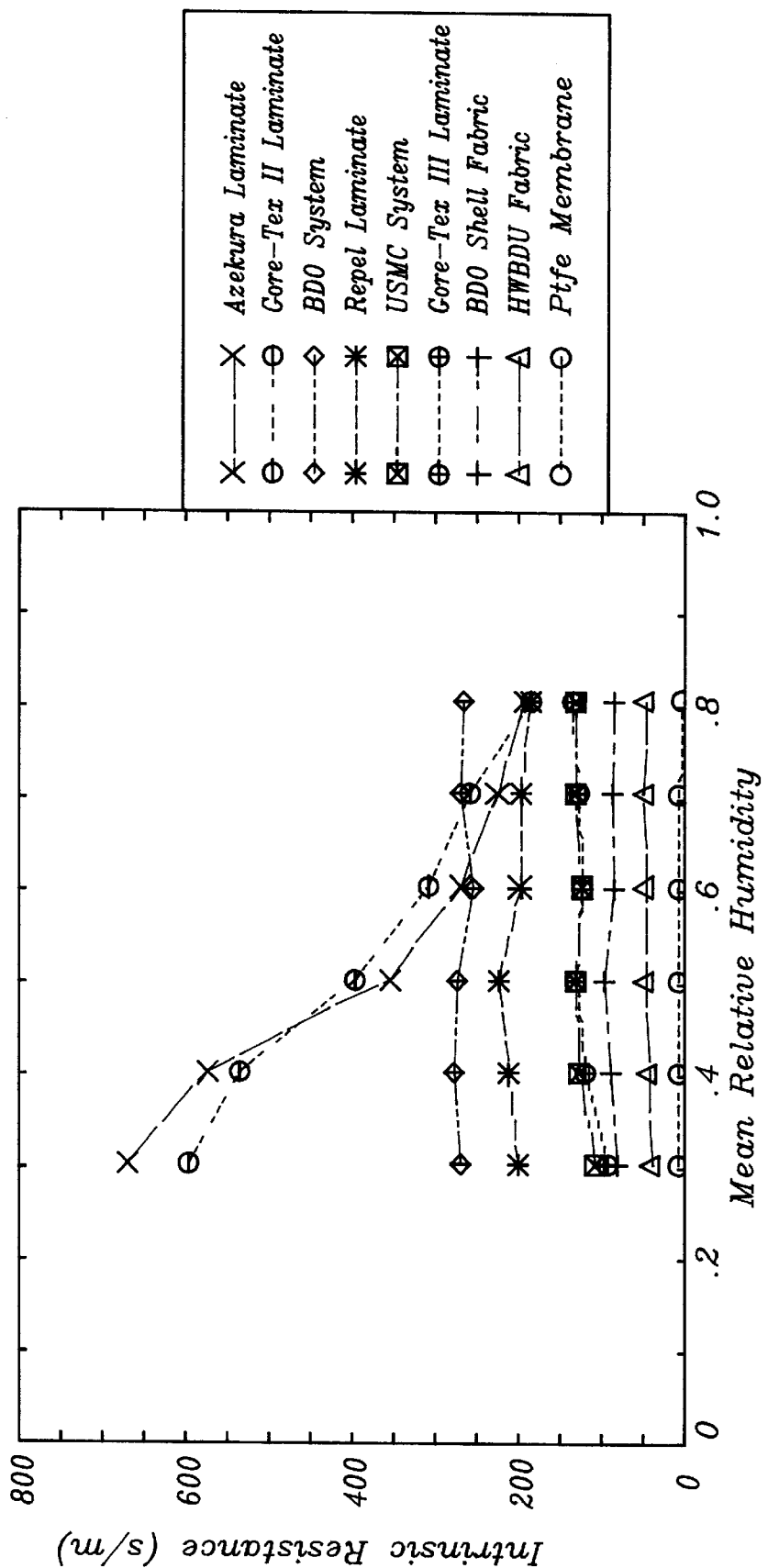
FIG. 4 is a plot of the intrinsic resistance as a function of average relative humidity for a variety of porous materials that were retained by the cell of FIG. 2 and tested by a method of the present invention.

To further illustrate the results generated by cell 10, three different classes of material were tested to determine transport by diffusion. They are 1) permeable fabrics, 2) microporous fabric-laminated membranes, and 3) hydrophilic nonporous fabrics laminated membranes. The diffusion resistance of each of these materials is calculated using the equations above. The intrinsic mass transfer resistance of each sample is obtained by subtracting the boundary layer resistance (100 s/m) from the total resistance measured in the test. The results of the tests for the aforementioned set of materials is shown in terms of an average relative humidity at the membrane. This approach is often used for materials that exhibit concentration-dependent permeation behavior. When using this approach, it is assumed that the average of the relative humidities of the two gas streams flowing into flow inlets 36 and 38 of the cell 10 could be related back to the water content of the sample estimated from a water vapor isotherm. However, this definition neglects the influence of the resistance of the boundary air layer, which further decreases the concentrations at the surfaces of the hydrophilic materials and neglects the variation in vapor concentration along the sample. A log mean average concentration/water content in the sample would be a more appropriate factor to use. However, it has been found that the average relative humidity method will be sufficient to illustrate the general trend of material behavior. FIG. 4 shows a plot of measured intrinsic log-mean diffusion resistance as a function of average relative humidity on the two sides of the test sample. As shown in FIG. 4, the fabrics and microporous membrane laminates show a fairly constant mass transfer resistance that is relatively independent of the test conditions. The two hydrophilic laminated membranes exhibit a relatively greater variation in their measured mass transfer resistance in contrast to the microporous membrane laminates. However, the wide variations in the measured mass transfer resistance of the two hydrophilic laminated membranes also depends upon the test conditions utilized.

2. Determining Diffusion and Convection

Figure 5:
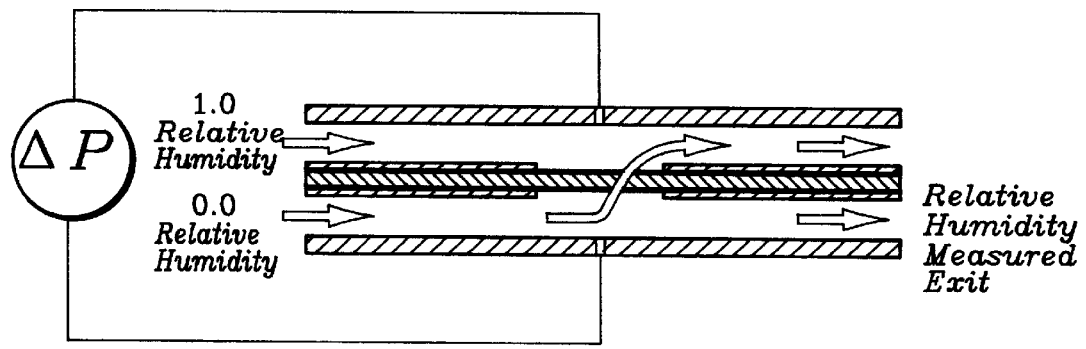
FIG. 5 is a diagram that illustrates gas flow through the cell of FIG. 2 when measuring convection/diffusion properties of a sample of porous material.

Referring to FIG. 5, in another embodiment, the cell 10 is configured to permit measurement of transport that occurs by both diffusion and convection thereby allowing for the determination of an air permeability value in addition to the water vapor diffusion properties of the sample of porous material 50. Such a configuration is useful for determining transport properties of permeable fabrics.

In such an embodiment, a specific pressure drop is created across the sample 50 so that transport occurs across the sample by both diffusion (driven by concentration differences) and convection (driven by gas phase pressure differences). FIG. 5 shows how cell 10 is configured to be used in determining transport due to diffusion and convection. A gas is flowed into flow inlets 36 and 38 of cell 10. The gas flowing into flow inlet 36 has a predetermined relative humidity. Similarly, the gas flowing into flow inlet 38 has a predetermined relative humidity. In one embodiment, the gas flowing into the flow inlet 38 is at a relative humidity of 1.0 and the gas flowing into the flow outlet 38 is at a relative humidity of 0.0. However, it is to be understood that the gases flowing into the flow inlets 36 and 38 may be at other relative humidities. Measurements are taken as a function of pressure drop across the sample of porous material wherein the convective flow and pressure drop are gradually increased in stepwise increments. This is accomplished by gradually restricting the gas flow exiting the flow outlet of the lower portion 18. Restricting the flow outlet in this manner causes the pressure in one side of the cell 10 to be higher than the pressure in the other side thereby causing convective flow across the sample of porous material 50 in addition to the diffusion flux taking place due to the concentration gradients. When implementing the aforementioned test, the electronic mass flow meter 83 (see FIG. 1) is connected to the flow outlet of portion 18 of the cell 10, as shown in FIG. 1, to record the mass flow rate of gas through the sample of porous material 50. The computer 62 produces a plot or curve of measured relative humidity at the flow outlet of the bottom portion 18 of cell 10 as a function of pressure drop across the sample of porous material 50. In a similar manner, an opposite pressure differential can be produced by restricting flow at the outlet of the top portion 12 of the cell 10.

Figure 6:
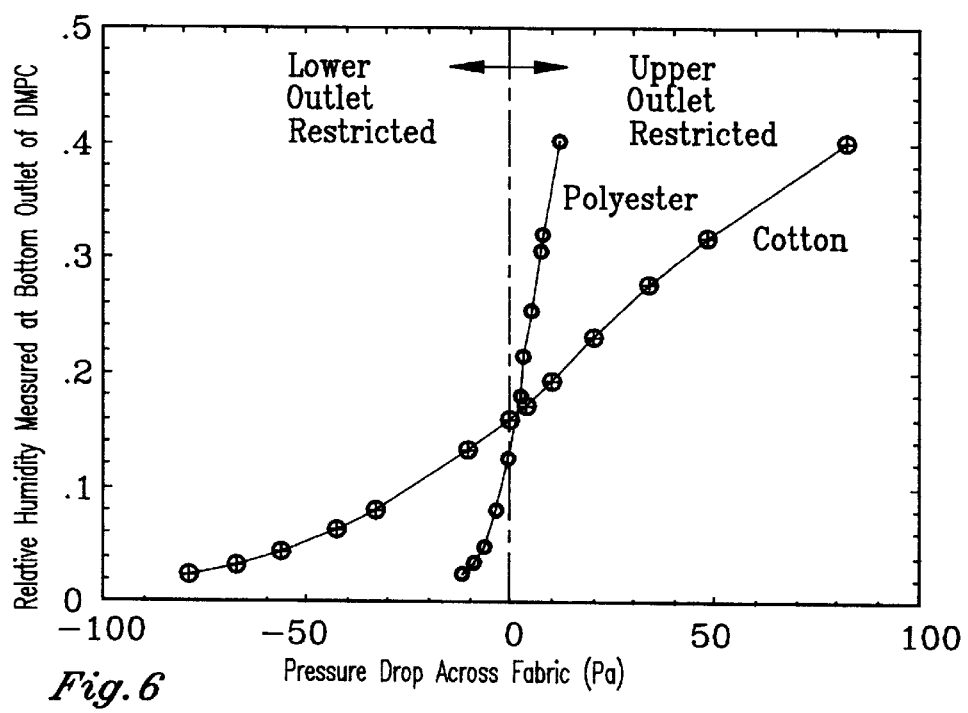
FIG. 6 is a plot of relative humidity, measured at an outlet of the cell of FIG. 2, as a function of pressure drop across a cotton fabric and a polyester fabric.

The system 60 shown in FIG. 1 and the cell 10, as configured in FIG. 5, was used to measure relative humidity at the flow outlet of the upper portion 12 as a function of pressure drop for a single layer of cotton and a single layer of polyester. The results of these tests are shown in FIG. 6. Cotton fabrics and the polyester fabrics have substantially identical diffusion resistances but have significantly different air permeability properties. Thus, when the cotton and polyester fabrics are tested under the conditions of the same pressure drop, there is significantly more convective flow through the polyester fabric than through the cotton fabric.

Figure 7:
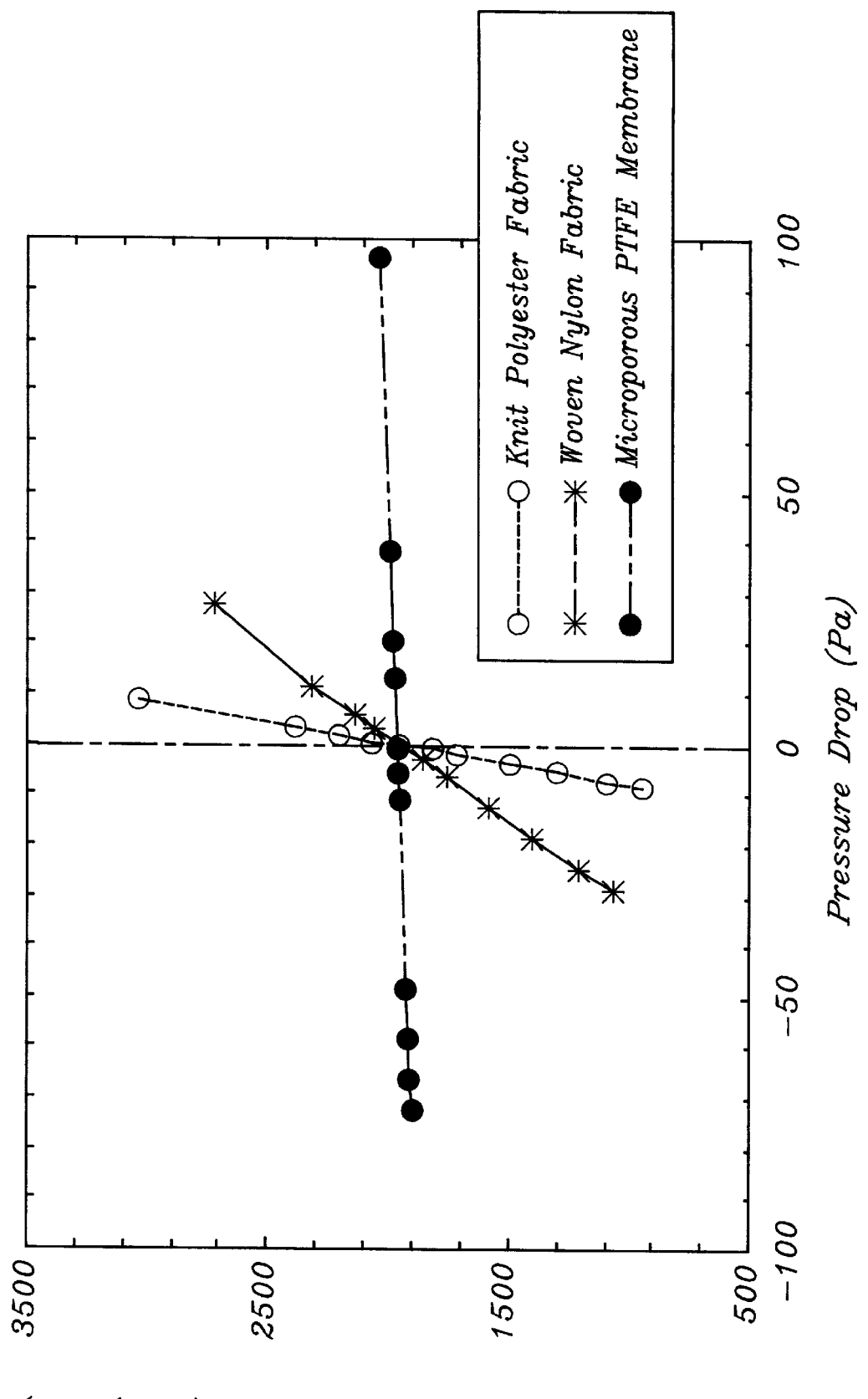
FIG. 7 is a plot of flow rate as a function of pressure drop for three different materials, each material being retained by the cell of FIG. 2.
Figure 8:
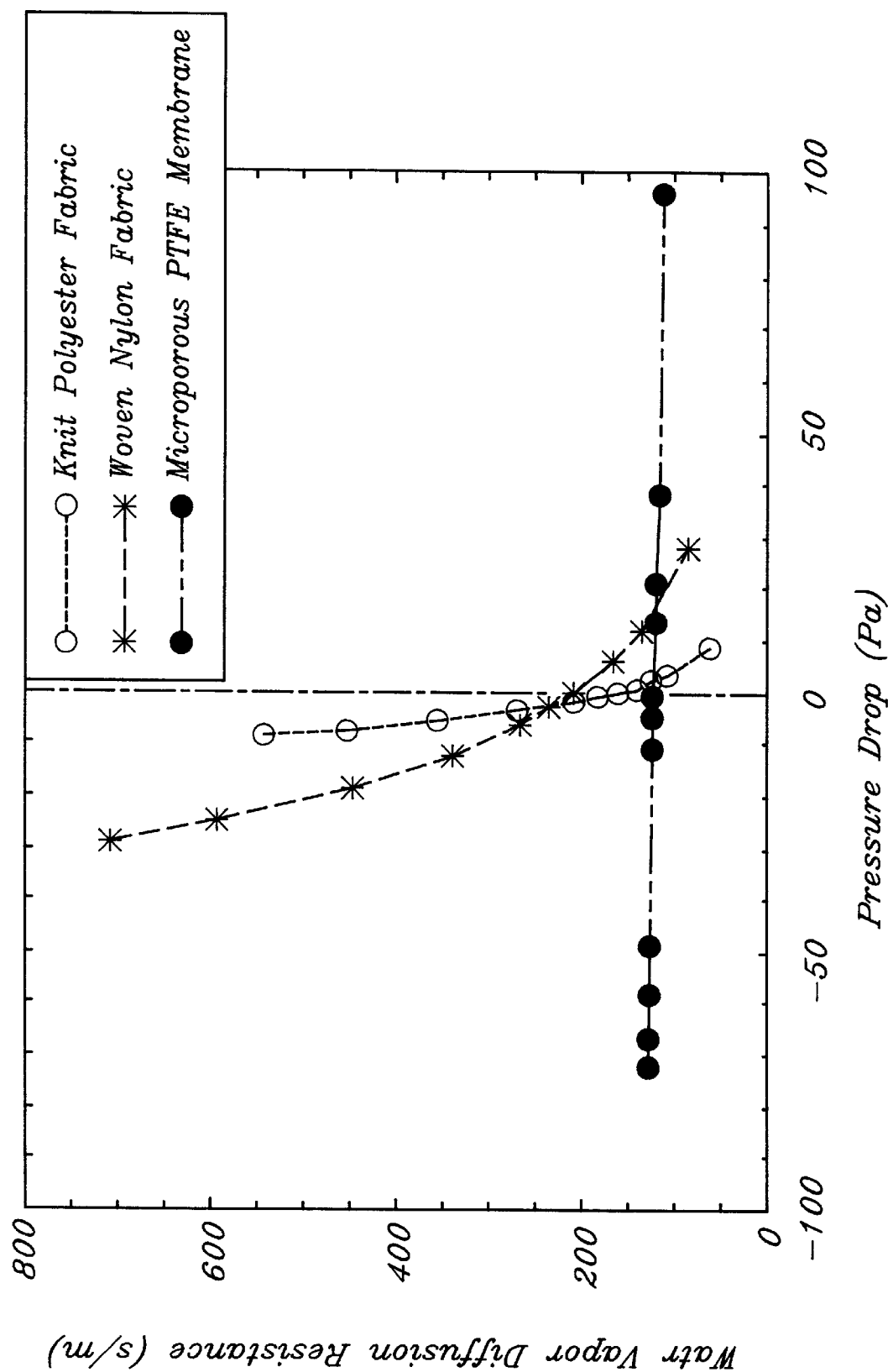
FIG. 8 is a plot of water vapor diffusion as a function of pressure drop for three different samples of porous materials, each sample being retained by the cell of FIG. 2.

FIGS. 7 and 8 show the measurements for the following three materials: (i) a microporous polytetrafluoethylene (PTFB) membrane with a relatively low water vapor diffusion resistance and a relatively high resistance to convective gas flow (relatively low air permeability), (ii) a knit polyester fabric with a slightly greater resistance to water vapor diffusion and a relatively low air flow resistance (high air permeability), and (iii) a woven nylon fabric with relatively higher water vapor diffusion resistance and an air flow resistance between the PTFE membrane and the knit polyester fabric. FIG. 7 shows flow rate as a function of pressure drop and is directly related to the air permeability of the material under test. The greater the slope of the line for a given material, the greater the air permeability of the material under test. As shown in FIG. 7, the microporous polytetrafluoethylene (PTFE) membrane has a relatively low air permeability (high flow resistance), the knit polyester fabric has a relatively high air permeability, and the woven nylon fabric is between the (PTFE) membrane and the woven fabric.

Figure 9:
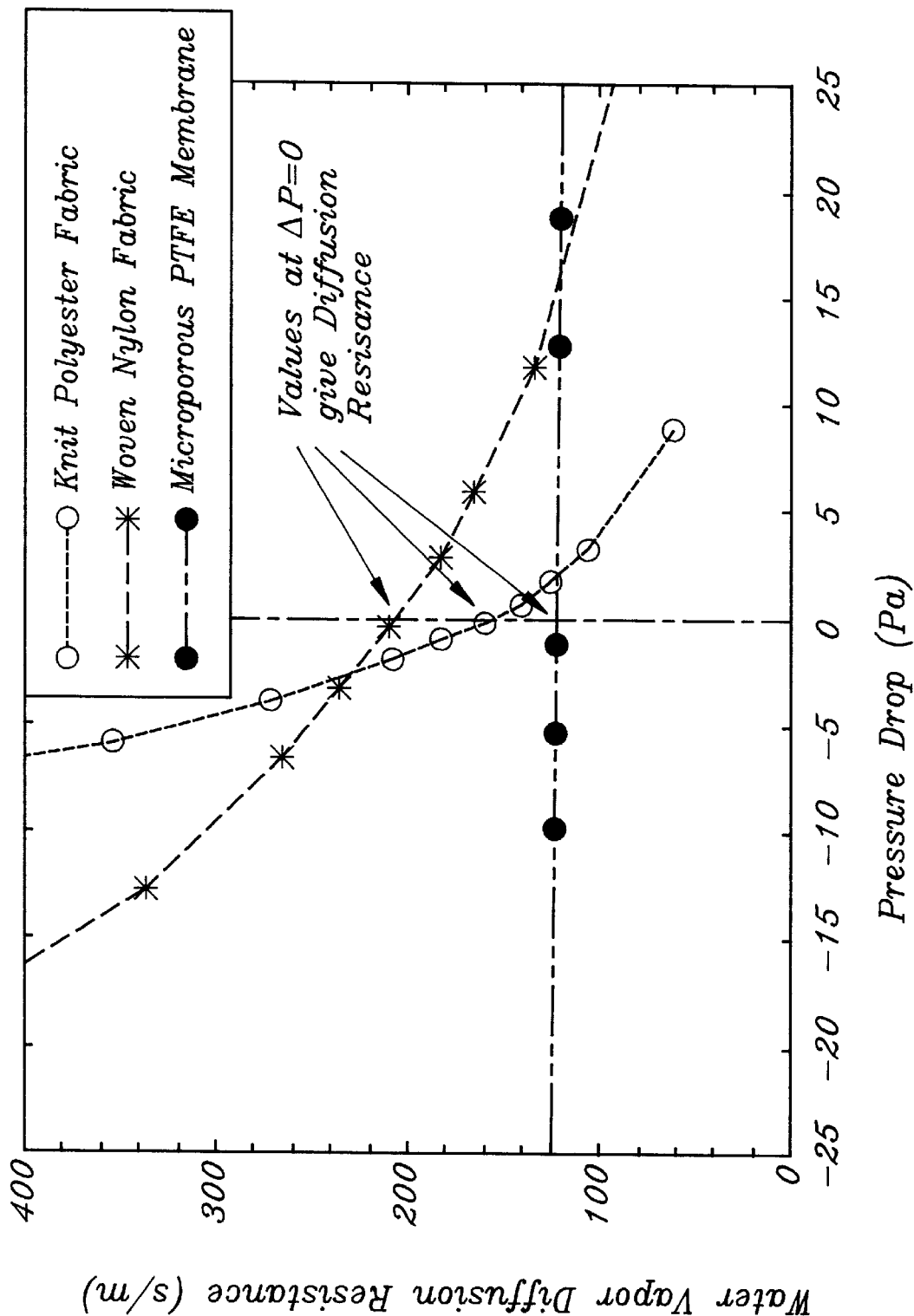
FIG. 9 is a plot illustrating the intersection of each curve shown in FIG. 8 with a vertical line representing ΔP=0.

FIG. 8 shows the apparent water vapor diffusion resistance as a function of pressure drop. This plot illustrates the interaction of convective and diffusive transport. FIG. 9 shows the intersection of each material's curve, shown in FIG. 8, with the $\Delta P=0$ point. The point of intersection defines the true water vapor diffusion value for that particular material. As shown in FIG. 9, the PTFE membrane has the lowest diffusion resistance, followed by the knit polyester, with the nylon fabric having the highest diffusion resistance. This PTFE membrane has a diffusion resistance of about 6–8 s/m. Thus, the boundary layer resistances in this particular configuration of the cell 10 (defined by flow rates and flow geometry) are approximately 115 s/m. Therefore, the true diffusion resistance of each material is equal to the difference between its total resistance from FIG. 9 and the boundary layer resistance. The resulting intrinsic diffusion resistances are 6 s/m for the PTFE membrane, 96 s/m for the nylon fabric, and 36 s/m for the polyester fabric. Since the aforementioned materials differ greatly in their air permeability properties, the change in apparent diffusion resistance as the pressure drop increases is quite different for the various materials. The PTFE membrane has a nearly constant diffusion resistance due to its low air permeability. As a result of the polyester fabric's high air permeability, even at very low pressure drops, e.g. 10 Pa, its apparent diffusion resistance is less than that of the PTFE membrane.

It has been found that the ability to conduct testing over a range of pressure drops increases the accuracy of the water vapor diffusion value and that slight variations in pressure drop across a sample of porous material with a high permeability will greatly influence the measured water vapor diffusion resistance. Conventional diffusion tests methods that do not control or monitor the convective flow through the sample of porous material are prone to measurement and ranking errors caused by air flow through the sample. The characteristic curve shown in FIG. 9, which illustrates the interaction between diffusive and convective transport, is significantly more realistic in terms of the transport processes taking place in clothing systems wherein both modes of transport occur simultaneously.

Operating cell 10 in the diffusion/convection mode provides plots of pressure drop versus either mass flow rate or volumetric flow rate (see FIG. 7). The volumetric flow rate is the most convenient to use, so the permeability constant may be found from the formula:

$$k_D = (\mu Q/A)(\Delta x/\Delta p) \qquad (7)$$

wherein:

$\mu$=gas viscosity ($17.84 \times 10^{-6}$ kg/m-s for $N_2$ at 20° C.);
Q=total volumetric flow rate ($m^3/s$);
A=apparent sample flow area ($1.0 \times 10^{-3}$ $m^2$ for cell 10);
$\Delta x$=thickness (m); and
$\Delta p$=pressure drop across sample ($N/m^2$ or Pa).

For textiles, although thickness measurements appear simple, they are often problematic, and can be a large source of error if they are incorporated into reported measurements of Darcy permeability. Thus, it is preferable to present the pressure-drop/flow rate results in terms of an apparent flow resistance defined as:

$$R_D = (A\Delta p/\mu Q_{total}) \qquad (8a)$$

wherein:

$R_D$=apparent Darcy flow resistance ($m^{-1}$).
The computer 62 determines the Darcy permeability from the apparent flow resistance using the following formula:

$$k_D = \Delta x/R_D \qquad (8b)$$

The volumetric flow rate shown in FIG. 7, measured by the electronic mass flow meter 83, is the equivalent volumetric flow rate at the reference temperature ($T_o$) of 0° C. (273.15 K), and reference atmospheric pressure ($p_o$) of $1.01325 \times 10^5$ Pa. The actual volumetric flow rate at a given temperature may be found from the mass flow rate ($Q_o$) indicated by the electronic mass flow meter 83, the ambient temperature ($T_a$), and the ambient pressure of the actual flow ($P_a$). The pressure correction is negligible ($P_o/P_a \approx 1$), so only the temperature correction needs to be made. The correction to obtain the actual volumetric flow rate ($Q_{total}$)=from the indicated mass flow rate ($Q_o$) is:

$$Q_{total} = Q_o(T_a/T_o)(p_o/p_a) \approx Q_o(T_a/T_o) \qquad (9)$$

The quantity ($\Delta p/\mu Q_{total}$) is equal to the inverse of the slopes of the curves shown in FIG. 7 (after correction to the proper temperature as shown above). Thus, the air flow area and gas viscosity are determined according to equation given above. For the three materials shown in FIG. 7, the equivalent air flow resistance is $2.78 \times 10^7$ m$^{-1}$ for the polyester fabric, $1.14 \times 10^8$ m$^{-1}$ for the nylon fabric, and $4.25 \times 10^9$ m$^{-1}$ for the PTFE microporous membrane. These values agree with those obtained previously for these materials by conventional methods. If the material thickness is known, the Darcy permeability (usually reported in units of m$^2$) can be found from the apparent flow resistance represented by formula (8a) above.

The convection/diffusion test method is most appropriate for air permeable materials such as porous textiles or fabrics, membranes or foams and can also be used for air-impermeable materials. The ability to use the convection/diffusion test method in accordance with the present invention for air-impermeable materials facilitates showing the convective flow versus the diffusive flow. Furthermore, the convection/diffusion test method of the present invention facilitates screening a relatively large number of samples, particularly developmental materials, since it gives an air permeability and a water vapor diffusion value from a single test.

3. Measuring Pure Convective Gas Flow Properties

Figure 10:
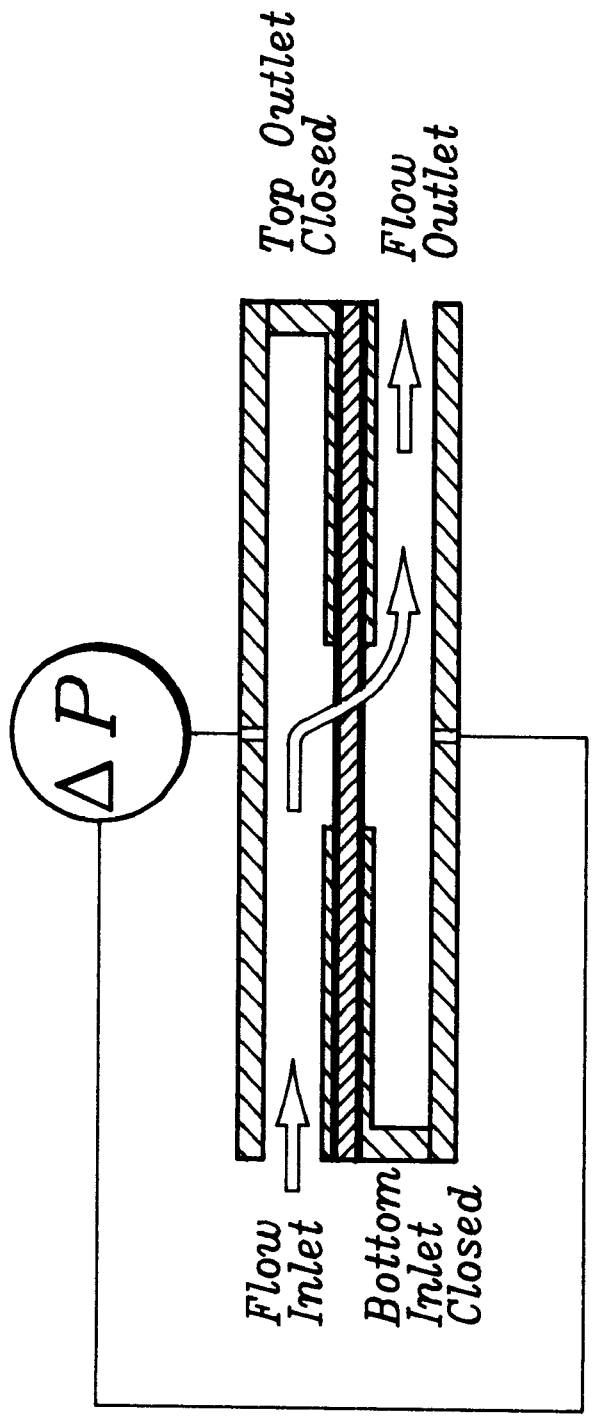
FIG. 10 is a diagram illustrating how the cell of FIG. 2 is configured for measuring humidity-dependent air permeability of a sample of porous materials.
Figure 11B:
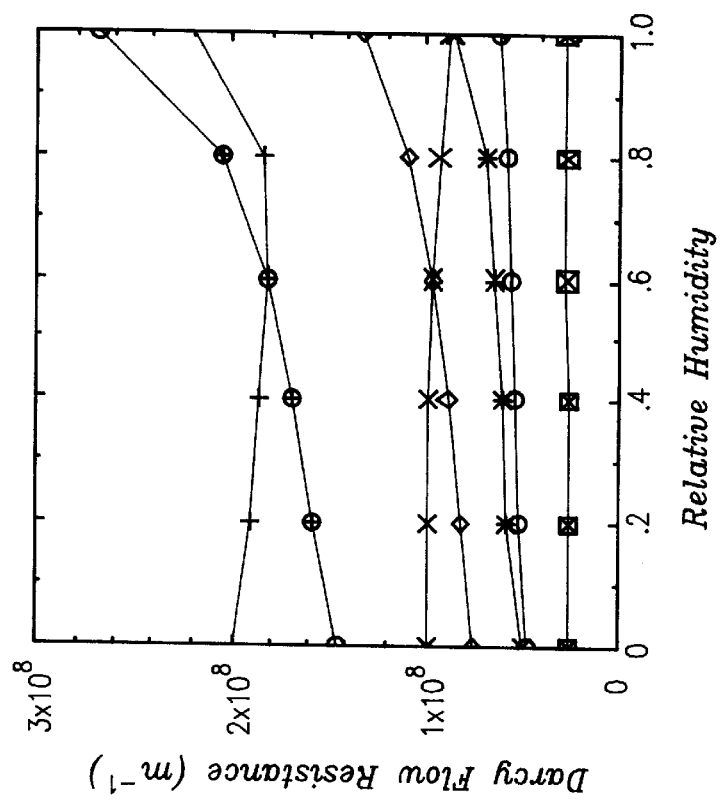
FIG. 11b is a plot of flow resistance of samples of seven fabrics, delineated in FIG. 8a, as a function of relative humidity, each sample of fabric being retained by the cell of FIG. 2 configured as shown in FIG. 7.
Figure 11A:
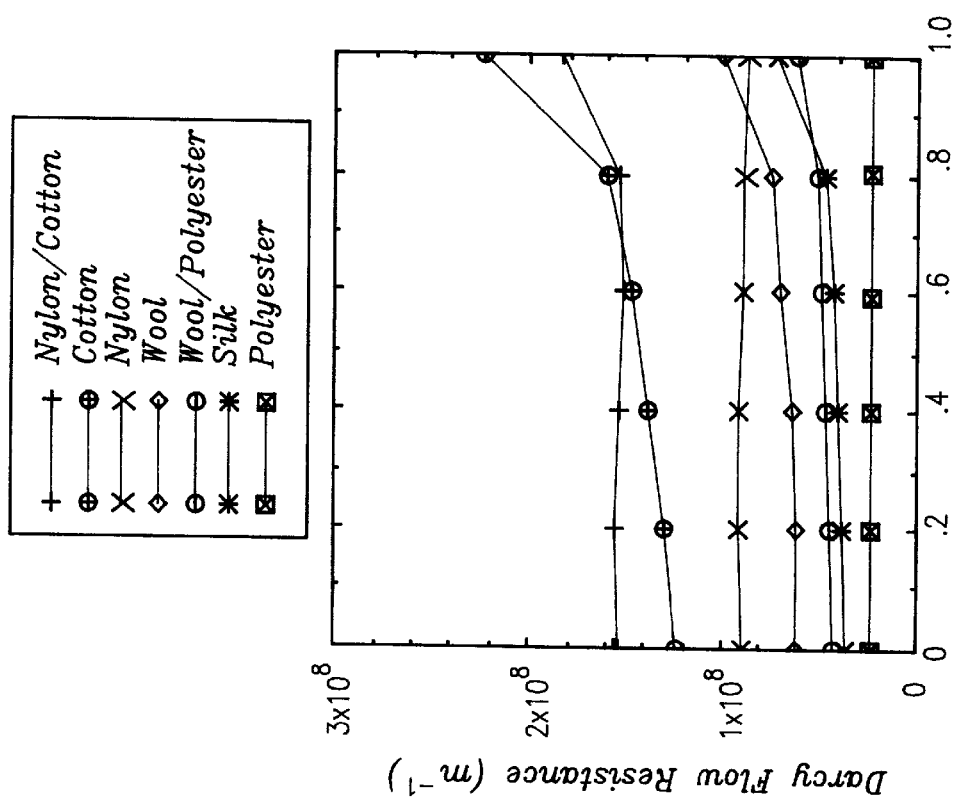
FIG. 11a is a plot of flow resistance of samples of seven fabrics as a function of relative humidity as determined in a conventional air-permeability flow cell.
Figure 12:
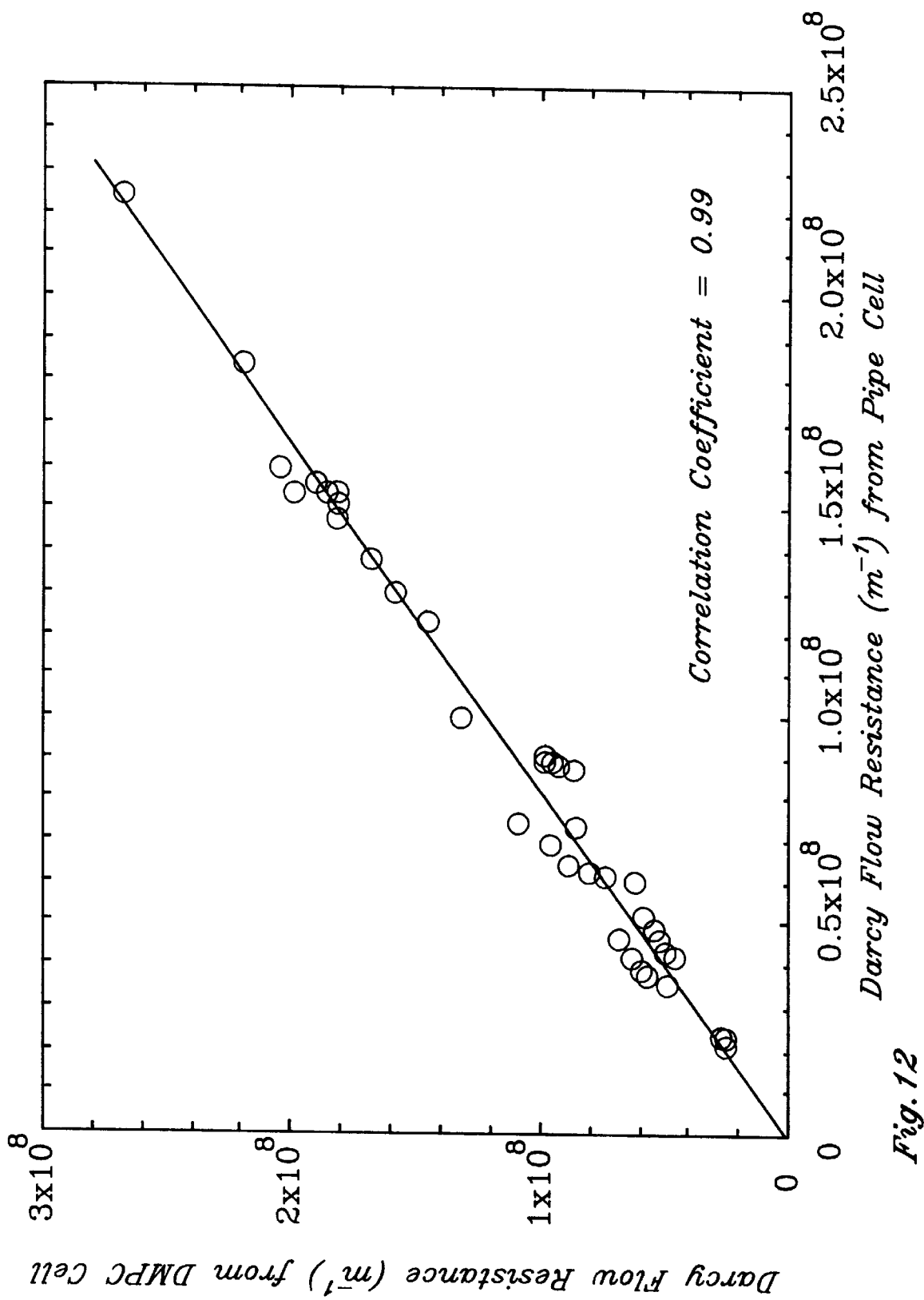
FIG. 12 is a plot illustrating the correlation between Darcy flow resistance measured by a conventional pipe cell and the Darcy flow resistance measured by the cell shown in FIG. 2.

In another embodiment, the cell 10 is configured as an air permeability cell to measure pure convective gas flow properties of porous materials. FIG. 10 shows the configuration of the cell 10 for measuring the pure convective gas flow properties. In such a configuration, the flow of gas into the flow inlet 38 is set to zero by closing the flow inlet 38. This can be accomplished setting the flow controllers 72 and 74 to zero. The flow outlet of the upper portion 12 is also closed using valve 110. The computer 62, using the known input gas flow rate and measured pressure drop, determines the permeability constant and the Darcy flow resistance from equation (8a) shown above. To illustrate the reliability of measurements derived from using cell 10 of the present invention, a comparison was made between measurements derived from a conventional air-permeability cell and cell 10. FIG. 11a shows the Darcy flow resistance of seven (7) fabrics, as a function of relative humidity, measured using a conventional air-permeability cell. FIG. 11b shows the Darcy flow resistance of the aforementioned seven (7) fabrics, as a function of relative humidity, measured using cell 10 of the present invention. FIG. 12 is a plot illustrating the correlation between Darcy flow resistance measured by a conventional pipe cell and the Darcy flow resistance measured by the cell 10 of the present invention.

The method and cell of the present invention have numerous advantages in comparison to conventional methods and devices. For example, the diffusion and convection flow properties may be determined without changing the samples of porous material under test thereby increasing the number of tests that can be done per unit of time. As a result, testing can be completed in relatively less time than conventional techniques.

Thus, the cell and method of the present invention achieves the objects set forth above. Specifically, the cell and method of the present invention:

a) provides for rapid determination of the transport properties of textiles or porous fabrics during the manufacturing process;
b) provides accurate and consistent measurements;
c) allows a plurality of tests to be conducted on the same sample of porous material thereby decreasing the amount of time necessary to conduct such tests; and
d) can be implemented at a relatively low cost.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:

1. A cell for retaining a sample of porous material comprising:

a first portion comprising an exterior side and an interior side, the first portion having a substantially longitudinally extending channel formed in the interior side, the first portion having at least one port extending from the exterior side to the interior side and in communication with the channel, the first portion further comprising a flow inlet and a flow outlet in communication with the channel;

a first clamping plate having a first side for contacting the interior side of the first portion and a second side for contacting a sample of porous material, the first clamping plate having an opening that is substantially aligned with the channel of the first portion;

a second clamping plate having a first side, the second clamping plate further comprising a second side for contacting a sample of porous material, the second clamping plate having an opening that is substantially aligned with the opening of the first clamping plate; and a second portion having an exterior side and an interior side for contacting the first side of the second clamping plate, the second portion having a substantially longitudinally extending channel formed in the interior side of the second portion, the second portion further including at least one port extending from the exterior side of the second portion to the interior side of the second portion and in communication with the channel formed in the interior side of the second portion, the second portion further comprising a flow inlet and a flow outlet in communication with the channel of the second portion;

wherein each channel has a length of about 0.13 meter.

2. A cell for retaining a sample of porous material comprising:

a first portion comprising an exterior side and an interior side, the first portion having a substantially longitudinally extending channel formed in the interior side, the first portion having at least one port extending from the exterior side to the interior side and in communication with the channel, the first portion further comprising a flow inlet and a flow outlet in communication with the channel;

a first clamping plate having a first side for contacting the interior side of the first portion and a second side for contacting a sample of porous material, the first clamping plate having an opening that is substantially aligned with the channel of the first portion;

a second clamping plate having a first side, the second clamping plate further comprising a second side for contacting a sample of porous material, the second clamping plate having an opening that is substantially aligned with the opening of the first clamping plate; and a second portion having an exterior side and an interior side for contacting the first side of the second clamping plate, the second portion having a substantially longitudinally extending channel formed in the interior side of the second portion, the second portion further including at least one port extending from the exterior side of the second portion to the interior side of the second portion and in communication with the channel formed in the interior side of the second portion, the second portion further comprising a flow inlet and a flow outlet in communication with the channel of the second portion;

wherein each channel has a width of about 0.0025 meter.

3. A cell for retaining a sample of porous material comprising:

a first portion comprising an exterior side and an interior side, the first portion having a substantially longitudinally extending channel formed in the interior side, the first portion having at least one port extending from the exterior side to the interior side and in communication with the channel, the first portion further comprising a flow inlet and a flow outlet in communication with the channel;

a first clamping plate having a first side for contacting the interior side of the first portion and a second side for contacting a sample of porous material, the first clamping plate having an opening that is substantially aligned with the channel of the first portion;

a second clamping plate having a first side, the second clamping plate further comprising a second side for contacting a sample of porous material, the second clamping plate having an opening that is substantially aligned with the opening of the first clamping plate; and a second portion having an exterior side and an interior side for contacting the first side of the second clamping plate, the second portion having a substantially longitudinally extending channel formed in the interior side of the second portion, the second portion further including at least one port extending from the exterior side of the second portion to the interior side of the second portion and in communication with the channel formed in the interior side of the second portion, the second portion further comprising a flow inlet and a flow outlet in communication with the channel of the second portion;

wherein each channel has a depth of about 0.0025 meter.

4. A cell for retaining a sample of porous material comprising:

a first portion comprising an exterior side and an interior side, the first portion having a substantially longitudinally extending channel formed in the interior side, the first portion having at least one port extending from the exterior side to the interior side and in communication with the channel, the first portion further comprising a flow inlet and a flow outlet in communication with the channel;

a first clamping plate having a first side for contacting the interior side of the first portion and a second side for contacting a sample of porous material, the first clamping plate having an opening that is substantially aligned with the channel of the first portion;

a second clamping plate having a first side, the second clamping plate further comprising a second side for contacting a sample of porous material, the second clamping plate having an opening that is substantially aligned with the opening of the first clamping plate; and a second portion having an exterior side and an interior side for contacting the first side of the second clamping plate, the second portion having a substantially longitudinally extending channel formed in the interior side of the second portion, the second portion further including at least one port extending from the exterior side of the second portion to the interior side of the second portion and in communication with the channel formed in the interior side of the second portion, the second portion further comprising a flow inlet and a flow outlet in communication with the channel of the second portion;

wherein each channel has a depth of about 0.005 meter.

5. A cell for retaining a sample of porous material comprising:

a first portion comprising an exterior side and an interior side, the first portion having a substantially longitudinally extending channel formed in the interior side, the first portion having at least one port extending from the exterior side to the interior side and in communication with the channel, the first portion further comprising a flow inlet and a flow outlet in communication with the channel;

a first clamping plate having a first side for contacting the interior side of the first portion and a second side for contacting a sample of porous material, the first clamping plate having an opening that is substantially aligned with the channel of the first portion;

a second clamping plate having a first side, the second clamping plate further comprising a second side for contacting a sample of porous material, the second clamping plate having an opening that is substantially aligned with the opening of the first clamping plate; and a second portion having an exterior side and an interior side for contacting the first side of the second clamping plate, the second portion having a substantially longitudinally extending channel formed in the interior side of the second portion, the second portion further including at least one port extending from the exterior side of the second portion to the interior side of the second portion and in communication with the channel formed in the interior side of the second portion, the second portion further comprising a flow inlet and a flow outlet in communication with the channel of the second portion;

wherein the opening in each of the clamping plates has an area of about 0.001 square meter.

6. The cell according to claim 3 wherein the opening in each of the clamping plates has a substantially square shape.

7. The cell according to claim 3 wherein the opening in each of the clamping plates is substantially centrally located.

8. The cell according to claim 3 wherein the port formed in the first portion is substantially aligned with the port formed in the second portion.

9. The cell according to claim 3 wherein the first and second portions and the first and second clamping plates are fabricated from a corrosion-resistant material.

10. The cell according to 3 wherein the first and second portions and the first and second clamping plates are substantially square in shape.

11. The cell according to claim 3 wherein each channel of the first and second portions has a pair of lengthwise ends, the flow inlet of the first portion being adjacent one end of the channel of the first portion and the flow outlet of the first portion being adjacent the other end of the channel of the first portion, the flow inlet of the second portion being adjacent one end of the channel of the second portion and the flow outlet of the second portion being adjacent the other end of the channel of the second portion.

12. The cell according to claim 3 wherein the at least one port of the first portion comprises a plurality of longitudinally arranged ports and the at least one port of the second portion comprises a plurality of longitudinally arranged ports.

13. The cell according to claim 3 wherein the flow inlet and flow outlet of the first portion are substantially coaxially aligned and the flow inlet and flow outlet of the second portion are substantially coaxially aligned.

14. A method for measuring the pure diffusion transport properties of a sample of porous material comprising:
   (a) providing a cell for retaining the sample of porous material, the cell comprising (i) a first portion comprising an exterior side and an interior side, the first portion having a substantially longitudinally extending channel formed in the interior side, the first portion having at least one port extending from the exterior side to the interior side and in communication with the channel, the first portion further comprising a flow inlet and a flow outlet in communication with the channel, (ii) a first clamping plate having a first side for contacting the interior side of the first portion and a second side for contacting a sample of porous material, the first clamping plate having an opening that is substantially aligned with the channel of the first portion, (iii) a second clamping plate having a first side, the second clamping plate further comprising a second side for contacting a sample of porous material, the second clamping plate having an opening that is substantially aligned with the opening of the first clamping plate, and (iv) a second portion having an exterior side and an interior side for contacting the first side of the second clamping plate, the second portion having a substantially longitudinally extending channel formed in the interior side of the second portion, the second portion further including at least one port extending from the exterior side of the second portion to the interior side of the second portion and in communication with the channel formed in the interior side of the second portion, the second portion further comprising a flow inlet and a flow outlet in communication with the channel of the second portion;
   (b) flowing gas streams that represent different porous sample medium conditions into the flow inlets of the first and second portions, each of the different sample conditions represented, respectively, by one of a gas stream having a dry gas portion, a water-saturated gas portion and a predetermined relative humidity;
   (c) maintaining the pressure drop across the sample of porous material so that transport occurs substantially by pure diffusion;
   (d) measuring the flux of water vapor diffusing through the sample of porous material;
   (e) varying the relative humidity of the gas streams flowing into the flow inlets of the first and second portions; and
   (f) repeating steps (b)–(e) to include respective measurements for each of the above stated porous sample medium conditions including a dry gas portion, a water-saturated portion, and a sequential set of different predetermined relative humidities.

15. The method according to claim 14 wherein step (d) comprises the steps of:
   (a) measuring the temperature of the gas streams flowing into the flow inlet of the first and second portions;
   (b) measuring the water concentration of the gas streams flowing into the flow inlets of the first and second portions; and
   (c) measuring the water concentration of the gas streams flowing from the flow outlets of the first and second portions.

16. The method according to claim 15 further comprising the step of determining the water vapor concentration of each gas stream flowing through the channels of the first and second portion by determining the ratio of the mass flows of the water-saturated portion and the dry portion of the gas streams.

17. The method according to claim 16 further comprising the step of determining the water vapor concentration in the gas streams flowing from the flow outlets by converting the relative humidity values and temperature to water vapor concentration.

18. The method according to claim 14 wherein step (c) comprises the steps of:
   maintaining the pressure across the sample of porous material at a zero pressure drop; and
   monitoring the pressure across the sample of porous material.

19. The method according claim 18 wherein the monitoring step comprises measuring the pressure differential pressure at the ports of the first and second portions.

20. A method for measuring the diffusion and convection transport properties of a sample of porous material comprising:
   (a) providing a cell for retaining the sample of porous material, the cell comprising (i) a first portion comprising an exterior side and an interior side, the first portion having a substantially longitudinally extending channel formed in the interior side, the first portion having at least one port extending from the exterior side to the interior side and in communication with the channel, the first portion further comprising a flow inlet and a flow outlet in communication with the channel, (ii) a first clamping plate having a first side for contacting the interior side of the first portion and a second side for contacting a sample of porous material, the first clamping plate having an opening that is substantially aligned with the channel of the first portion, (iii) a second clamping plate having a first side, the second clamping plate further comprising a second side for contacting a sample of porous material, the second clamping plate having an opening that is substantially aligned with the opening of the first clamping plate, and (iv) a second portion having an exterior side and an interior side for contacting the first side of the second clamping plate, the second portion having a substantially longitudinally extending channel formed in the interior side of the second portion, the second portion further including at least one port extending from the exterior side of the second portion to the interior side of the second portion and in communication with the channel formed in the interior side of the second portion, the second portion further comprising a flow inlet and a flow outlet in communication with the channel of the second portion;

(b) flowing gas streams that represent different porous sample medium conditions into the flow inlets of the first and second portions, each of the different sample conditions represented, respectively, by one of a gas stream having a dry gas portion, a water-saturated gas portion and a predetermined relative humidity;

(c) creating a pressure drop across the sample of porous material so that transport occurs by diffusion and convection;

(d) measuring the relative humidity of the nitrogen streams flowing from the flow outlets of the upper and lower portions;

(e) increasing the pressure drop across the sample of porous material;

(f) measuring the mass flow rate of gas leaving the lower portion; and (f) repeating steps (b)–(e) to include respective measurements for each of the above stated porous sample medium conditions including a dry gas portion, a water-saturated portion, and a sequential set of different predetermined relative humidities.

21. The method according to claim 20 wherein step (b) further comprises the steps of:
setting the relative humidity of the gas stream flowing into the flow inlet of the upper portion to about 1.0; and
setting the relative humidity of the gas stream flowing into the flow inlet of the lower portion to about 0.0.

22. The method according to claim 20 wherein step (e) comprises the step of gradually restricting the flow outlet of the second portion so as to cause the pressure within the channel of the second portion to be higher than the pressure in the channel of the first portion.

23. The method according to claim 20 wherein step (f) further comprises the step of providing an apparatus for measuring the mass flow rate of gases through the sample of porous material.

24. A method for measuring the humidity-dependent convective transport properties of a sample of porous material comprising:

(a) providing an cell for retaining the sample of porous material, the cell comprising (i) a first portion comprising an exterior side and an interior side, the first portion having a substantially longitudinally extending channel formed in the interior side, the first portion having at least one port extending from the exterior side to the interior side and in communication with the channel, the first portion further comprising a flow inlet and a flow outlet in communication with the channel, (ii) a first clamping plate having a first side for contacting the interior side of the first portion and a second side for contacting a sample of porous material, the first clamping plate having an opening that is substantially aligned with the channel of the first portion, (iii) a second clamping plate having a first side, the second clamping plate further comprising a second side for contacting a sample of porous material, the second clamping plate having an opening that is substantially aligned with the opening of the first clamping plate, and (iv) a second portion having an exterior side and an interior side for contacting the first side of the second clamping plate, the second portion having a substantially longitudinally extending channel formed in the interior side of the second portion, the second portion further including at least one port extending from the exterior side of the second portion to the interior side of the second portion and in communication with the channel formed in the interior side of the second portion, the second portion further comprising a flow inlet and a flow outlet in communication with the channel of the second portion;

(b) closing the flow inlet of the second portion;

(c) closing the flow outlet of the first portion;

(d) flowing a gas stream that represents a different porous sample medium condition into the flow inlet of the first portion, each of the different sample conditions represented by the gas stream having, respectively, one of a dry gas portion, a water-saturated gas portion and a predetermined relative humidity;

(e) measuring the pressure drop across the sample of porous material as a function of flow rate and relative humidity;

(f) varying the relative humidity of the gas stream; and (g) repeating steps (b)–(f) to include respective measurements for each of the above stated porous sample medium conditions including a dry gas portion, a water-saturated portion, and a sequential set of different predetermined relative humidities.

25. The method according to claim 24 further comprising the step of measuring the relative humidity of the gas stream flowing from the flow outlet of the second portion.

26. The method according to claim 24 further comprising the step of determining the permeability constant for the sample of porous material.

27. The method according to claim 26 further comprising the step of determining the Darcy permeability and Darcy flow resistance from the apparent flow resistance of the porous material.

* * * * *